United States Patent [19]

Rosenbaum et al.

[11] Patent Number: 5,443,823
[45] Date of Patent: Aug. 22, 1995

[54] COMBINATION OF PYRIMIDINE DERIVATIVES AND OF SALICYLIC ACID DERIVATIVES FOR INDUCING AND STIMULATING THE GROWTH OF HAIR AND REDUCING ITS LOSS

[75] Inventors: Georges Rosenbaum, Asnieres; Michel Hocquaux, Paris, both of France

[73] Assignee: L'Oreal, Paris, France

[21] Appl. No.: 995,553

[22] Filed: Dec. 24, 1992

Related U.S. Application Data

[63] Continuation of Ser. No. 721,922, Jun. 21, 1991, abandoned, which is a continuation of Ser. No. 330,755, Mar. 30, 1989, abandoned.

[30] Foreign Application Priority Data

Mar. 31, 1988 [LU] Luxembourg ............... 87187

[51] Int. Cl.$^6$ ............................... A61K 7/06
[52] U.S. Cl. ................... 424/70.1; 424/489; 514/880; 514/944
[58] Field of Search ........... 424/70; 514/880, 881, 514/247, 256, 159, 161, 162

[56] References Cited

U.S. PATENT DOCUMENTS

| | | | |
|---|---|---|---|
| 4,559,328 | 12/1985 | Smerbeck et al. | 514/159 |
| 4,767,750 | 8/1988 | Jacquet et al. | 514/159 |
| 4,820,512 | 4/1989 | Grollier | 424/70 |

FOREIGN PATENT DOCUMENTS

| | | | |
|---|---|---|---|
| 2581542 | 5/1985 | France | |
| 2175902 | 12/1986 | United Kingdom | |
| 2207051 | 1/1989 | United Kingdom | A61K 7/06 |
| 8807361 | 10/1988 | WIPO | A61K 7/06 |

OTHER PUBLICATIONS

Chemical Abstracts, vol. 78, 1973, p. 37, No. 52753c.

Patent Abstracts of Japan, vol. 11, No. 115 (C-415) [2562] Apr. 10, 1987.

*Primary Examiner*—Thurman K. Page
*Assistant Examiner*—Sally Gardner
*Attorney, Agent, or Firm*—Jacobson, Price, Holman & Stern

[57] ABSTRACT

The combination comprises:
a) a component (A) containing a pyrimidine derivative of formula:

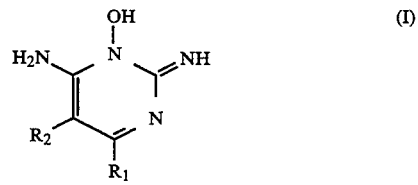

(I)

in which $R_1$ denotes

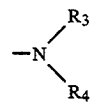

in which $R_3$ and $R_4$ denote hydrogen, alkyl, alkenyl, alkylaryl or cycloalkyl, $R_3$ and $R_4$ may also form a heterocyclic ring with the nitrogen atom to which they are linked, $R_2$ is hydrogen, alkyl, alkenyl, alkoxyalkyl, cycloalkyl, aryl, alkylaryl, arylalkyl, alkylarylalkyl, alkoxyarylalkyl or haloarylalkyl; and
b) a component (B) containing a salicylic acid derivative.

The components (A) and (B) forming part of the same single composition or being intended to be employed separately, either simultaneously or successively or at intervals of time, on the hair and the scalp.

11 Claims, No Drawings

COMBINATION OF PYRIMIDINE DERIVATIVES AND OF SALICYLIC ACID DERIVATIVES FOR INDUCING AND STIMULATING THE GROWTH OF HAIR AND REDUCING ITS LOSS

This application is a continuation of application Ser. No. 07/721,922, filed Jun. 21, 1991, now abandoned, which is a continuation of application Ser. No. 07/330,755, filed Mar. 30, 1989, now abandoned.

The invention relates to the combination of pyrimidine derivatives and of salicylic acid derivatives with a view to inducing and stimulating the growth of hair and reducing its loss.

The activity of hair follicles is cyclic. The active anagen phase, which lasts several years and during which the hair lengthens, is followed by a phase of rest (telogen) of a few months. At the end of this period of rest the hair falls out and another cycle begins again.

The head of hair is thus continually renewed; out of the 100,000 to 150,000 hairs which make up a head of hair, at any time approximately 10% are at rest and will therefore be replaced in a few months.

In almost all cases, the loss of hair appears in individuals who are genetically susceptible, and it affects men more particularly. Androgenetic alopecia is more particularly involved.

This alopecia is a disorder of the renewal of hair which, in a first stage, entails an acceleration of the cycle frequency at the expense of the quality of hair, and then of its quantity. There is a progressive depletion of hair due to regression of the so-called "terminal hair at the down stage". Regions are affected preferentially: temporal or frontal bays, among others, in men, and a diffuse alopecia of the crown is found in women.

It has already been proposed to employ compounds such as 6-amino-1,2-dihydro-1-hydroxy-2-imino-4-piperidinopyrimidine or minoxidil in compositions making it possible to reduce or to eliminate the effect of alopecia and to induce and to stimulate the growth of hair and to reduce its loss.

The Applicant has now found that combining salicylic acid derivatives with certain pyrimidine derivatives resulted surprisingly in an improved induction and stimulation of the growth of hair and an action on the retardation of hair loss, as well as a marked increase in cutaneous bioavailability and/or transcutaneous penetration.

The salicylic acid derivatives which are more particularly preferred according to the invention are known per se and are described more particularly in French Patent 2,581,542 in the case of their keratolytic properties.

The combination has been found to have an activity which is superior when compared with pyrimidine derivatives employed by themselves, the salicylic acid derivatives themselves having no effect on the growth of hair or on the retardation of hair loss.

The combination also makes it possible to ascertain a faster action in relation to the treatment of hair loss and makes it possible to use pyrimidine derivatives at lower concentrations to achieve a superior or equivalent effectiveness.

The Applicant has also found that, surprisingly, the combination of salicylic acid derivatives with pyrimidine derivatives greatly modified the solubility of pyrimidine derivatives and, in particular, offers the advantage of allowing a faster dissolution of the active substances consisting of pyrimidine derivatives.

This phenomenon of cosolubilization is especially advantageous insofar as it is produced with a derivative bearing a keratolytic activity and insofar as it makes it possible, as a result of a higher solubility, to obtain a better bioavailability and/or transcutaneous penetration.

In order to determine the effectiveness or the speed of action of the compositions for the treatment of alopecia, use is generally made of the trichogramor the phototrichogram which makes it possible to determine, inter alia, the percentage of hair in an anagen phase, relative to the hair in a telogen phase.

A subject of the invention consists, therefore, of the combination of pyrimidine derivatives and of salicylic acid derivatives with a view to inducing and stimulating the growth of hair and reducing its loss.

Another subject of the invention consists of cosmetic and/or pharmaceutical compositions containing these compounds.

A further subject of the invention is the multicompartment devices permitting the combination in accordance with the invention to be put to use.

Further subjects of the invention will become apparent on reading the description and the examples which follow.

According to this invention there is provided a combination of components that is effective for use in inducing and stimulating hair growth and for decreasing hair loss in which components are intended for use either as a composition comprising said components or as separate components that are used either simultaneously, successively or intermittently and in which the combination comprises:

a) a first component (A) comprising a physiologically acceptable medium and an effective amount of at least one pyrimidine derivative having the formula:

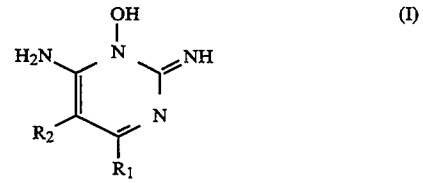

as well as acid addition salts there of physiologically acceptable acids, wherein $R_1$ represents a group having the formula

wherein $R_3$ and $R_4$ are selected from the group of substituents consisting of hydrogen, alkyl, alkenyl, alkylaryl and cycloalkyl or form a heterocyclic ring with the nitrogen to which they are each bound, which is unsubstituted or is substituted on the carbon atoms with one to three lower alkyl, hydroxyl, or alkoxy groups, and which is selected from the group of consisting of aziridinyl, azetidinyl, pyrrolidinyl, piperidyl, hexahydrolazepinyl, heptamethylenimine, octamethyleneimine, morpholine and 4-(lower)-alkyl-piperazidinyl groups, and wherein $R_2$ is selected from the group consisting of hydrogen, alkyl, alkenyl, alkoxyalkyl, cycloalkyl, aryl, alkylaryl, arylalkyl, alkylarylalkyl, alkoxyarylalkyl and haloarylalkyl; and (b) a second component (B) comprising a physiologically acceptable medium and at least one salicylic acid derivative or physiologically acceptable salts or esthers thereof having the formula

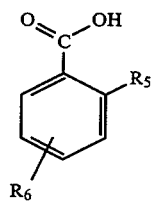

wherein $R_5$ is a hydroxyl or ester functional group having the formula:

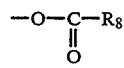

in which $R_8$ is saturated or unsaturated aliphatic radical containing from 1 to 15 carbon atoms, and wherein $R_6$ is a linear or branched alkyl or alkoxy radical containing from 1 to 18 carbon atoms or is a group having the formula

in which $R_7$ is selected from the group consisting of saturated aliphatic chains that contain from 1 to 11 carbon atoms and that may be linear, branched or cyclized, unsaturated chains having from 3 to 17 carbon atoms and one or more conjugated or unconjugated double bonds, and an aromatic nucleus linked to the carbonyl radical directly or through a saturated or unsaturated aliphatic chain containing from 2–7 carbon atoms, wherein any member of said group may be substituted with a substituent selected from the group consisting of one or more halogen atoms, one or more trifluoromethyl groups, and one or more hydroxyl groups, wherein said substituent is free form, is esterified with an acid containing from 1 to 6 carbon atoms, or is esterified by a carboxyl group, which is free or is esterified with a lower alcohol containing from 1 to 6 carbon atoms.

In the case of the compounds of formula (I), the alkyl or alkoxy groups preferably denote a group containing from 1 to 4 carbon atoms; the alkenyl group preferably denotes a group containing 2 to 5 carbon atoms; the aryl group preferably denotes phenyl and the cycloalkyl group preferably denotes a group containing 4 to 6 carbon atoms.

The preferred compounds of formula (I) are chosen more particularly from the compounds in which $R_2$ denotes hydrogen and $R_1$ denotes a group:

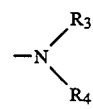

in which $R_3$ and $R_4$, independently of each other, denote hydrogen or a $C_1$–$C_4$ alkyl group or $R_3$ and $R_4$ form a piperidinyl ring. More particular mention may be made of the compound consisting of 6-amino-1,2-dihydro-1-hydroxy-2-imino-4-diethylaminopyrimidine and the compound consisting of 6-amino-1,2-dihydro and the compound consisting of 6-amino-1,2-dihydro-1-hydroxy-2-imino-4-piperidinopyrimidine, also called minoxidil. A preferred salt consists more particularly of sulphate.

In the case of the compounds of formula (II), the group $R_6$ is preferably in position 5 of the ring and it is preferably chosen from alkanoyl groups containing 2 to 12 carbon atoms and more particularly from the n-octanoyl, 3,3-dimethylbutyroyl, 2-propylpentanoyl, n-dodecanoyl, n-decanoyl and heptanoyl groups. The group $R_6$ may also be chosen from alkyl groups containing 1 to 18 carbon atoms and especially hexyl, octyl and decyl groups. The alkoxy groups are groups containing between 1 and 18 carbon atoms and are more particularly chosen from n-hexyloxy, n-heptyloxy and n-decyloxy groups.

The compounds which are particularly preferred are chosen from 5-n-octanoylsalicylic acid, 5-n-decanoylsalicylic acid, 5-n-dodecanoylsalicylic acid, 5-n-octylsalicylic acid, 5-n-heptyloxysalicylic acid and 4-n-heptyloxysalicylic acid or their physiologically acceptable salts or esters.

The pyrimidine derivatives of formula (I) are employed in the component (A) in proportions of between 0.05 and 10% by weight and, in particular, between 0.05 and 5% by weight and, preferably, between 0.5 and 4% by weight.

The salicylic acid derivatives corresponding to formula (II) are employed in the component B in proportions of between 0.05 and 10% by weight and in particular between 0.05 and 5% by weight.

The molar ratio of the pyrimidine derivatives of formula (I) to the salicyclic acid derivatives of formula (II) is more particularly between 1 and 10.

The Applicant has found that, by virtue of this combination, it was possible to dissolve a greater quantity of pyrimidine derivatives of formula (I) and more particularly of minoxidil, in the physiologically acceptable medium.

The physiologically acceptable medium for the components (A) and (B) is a medium which can be employed in pharmacy and in cosmetics and may consist of a mixture of water and of one or more organic solvents or of a mixture of physiologically acceptable organic solvents.

These compositions may be pressurized in aerosol devices in the presence of a propellant agent.

The solvents which may be employed more particularly are chosen from $C_1$–$C_4$ lower alcohols such as ethyl alcohol, isopropyl alcohol, tert-butyl alcohol, alkylene glycols such as propylene glycol, mono- and dialkylene glycol alkyl ethers such as, more particularly, ethylene glycol monoethyl ether, propylene glycol monomethyl ether and diethylene glycol monethyl ether.

The physiologically acceptable media may be thickened or not. Thickening and/or gelling agents which are well known in the state of the art are employed for thickening them, such as, more particularly, heterobiopolysaccharides like xanthan gum or scleroglucans, cellulose derivatives, and crosslinked or uncrosslinked acrylic polymers.

When employed in the aqueous medium, the solvents are preferably present in proportions of between 1 and 80% by weight relative to the total weight of the composition.

When employed, the thickeners are preferably present in proportions of between 0.1 and 5% by weight and in particular between 0.4 and 3% by weight relative to the total weight of each of the components (A) and (B) when these components are employed separately, or in relation to the total weight of the composition containing the components (A) and (B).

The compositions consisting either of either or both of the components (A) and (B) or of the composition containing both components (A) and (B) may also contain any other adjuvants which are usually employed in compositions intended for topical application for cosmetic or pharmaceutical use, and more particularly preserving agents, complexing agents, colorants, alkalifying or acidifying agents, anionic, cationic, nonionic or amphoteric surface-active agents or mixtures thereof, and anionic, cationic, nonionic or amphoteric polymers, as well as mixtures thereof. The pH of these compositions may vary between 4 and 9.

A preferred embodiment of the invention consists of employing the combination in the form of a composition containing the components (A) and (B); a composition of this kind forms another subject of the invention.

This embodiment is particularly advantageous because of the properties of cosolubilization of the compound of formula (II) in the compound of formula (I).

This composition contains the pyrimidine derivative of formula (I) in proportions of between 0.05 and 6% by weight relative to the total weight of the composition, and preferably between 0.1 and 5% by weight, and in particular between 0.5 and 2% by weight.

The salicylic acid derivatives of formula (II) are present in proportions of 0.05 to 10% by weight and preferably between 0.05 and 5% by weight.

Owing to the improved solubility characteristics, a composition of this kind may also be prepared just before use, when the components (A) and (B) are stored separately.

Another embodiment may consist in applying the components (A) and (B) separately, either simultaneously or in succession or after intervals of time.

When the components (A) and (B) are employed separately, the component (A) contains the pyrimidine derivatives of formula (I) either in dissolved form in the physiologically acceptable medium or else completely or partially suspended in this medium, in particular in a micronized form, that is to say in the form of particles with a particle size below 80 microns and preferably below 20 microns, and in particular below 5 microns.

In this case, the combination in accordance with the invention may be packaged in a multicompartment device, also called a "kit" or outfit, in which a first compartment contains the component (A) enclosing the pyrimidine derivatives of formula (I) in a physiologically acceptable medium and the second compartment containing the component (B) based on the salicylic acid derivative of formula (II).

As indicated above, the combination in accordance with the invention allows hair loss to be treated therapeutically by acting more particularly on the dysfunction of the biological mechanisms at the source of hair growth. The treatment may consist in performing a daily application of the composition containing the components (A) and (B) defined above, for a period of a few months, this being done at the rate of one application daily.

The Applicant has found that, by virtue of the combination in accordance with the invention, the cutaneous availability and the transcutaneous penetration were improved, which increased the effectiveness of the composition.

Furthermore, the composition also offers the advantage of being bacteriostatic.

The compositions in accordance with the invention also enable the hair to be treated cosmetically, that is to say to impart a greater vigour and better appearance thereto.

Another subject of the invention is the use of the combination such as defined above for the preparation of a medication intended for the treatment of alopecia, acting particularly on the dysfunction of the hair cycle.

The following examples are intended to illustrate the invention without, however, being limiting in nature.

EXAMPLE 1

A gel of the following composition is prepared:

| | |
|---|---|
| Minoxidil | 3 g |
| 5-n-Octanoylsalicylic acid | 0.55 g |
| Xanthan sold under the name Keltrol T by Kelco | 0.75 g |
| Ethyl alcohol | 50 g |
| Water q.s. | 100 g |

This composition is applied to the alopecic parts of the scalp.

EXAMPLE 2

A gel of the following composition is prepared:

| | |
|---|---|
| Minoxidil | 3.2 g |
| 5-n-Octanoylsalicylic acid | 2.25 g |
| Hydroxypropyl cellulose sold under the name Klucel G by Hercules | 2 g |
| Ethyl alcohol/propylene glycol (95/5) q.s. | 100 g |

This composition is applied to the alopecic parts of the scalp.

EXAMPLE 3

Two compositions (A) and (B) are prepared, packaged as a kit and containing, respectively:

| | |
|---|---|
| Composition (A): | |
| Minoxidil | 1.5 g |
| Propylene glycol | 20 g |
| Ethyl alcohol | 50 g |
| Water q.s. | 100 g |
| Composition (B): | |
| 5-n-Decanoylsalicylic acid | 0.4 g |
| Propylene glycol | 20 g |
| Ethyl alcohol | 50 g |
| Water q.s. | 100 g |

The composition (A) and the composition (B) are applied to the alopecic parts of the scalp at intervals of time, (A) in the morning and (B) in the evening or vice versa.

The compositions (A) and (B) may also be applied on alternate days ((A) 1 day out of 2, (B) 1 day out of 2).

EXAMPLE 4

Two compositions (A) and (B) are prepared, packaged as a kit and containing, respectively:

| Composition (A): | |
|---|---|
| Minoxidil | 2 g |
| Propylene glycol | 20 g |
| Ethyl alcohol | 50 g |
| Water q.s. | 100 g |
| Composition (B): | |
| 5-n-Dodecanoylsalicylic acid | 1.5 g |
| Ethyl alcohol/propylene glycol (95/5) q.s. | 100 g |

The compositions (A) and (B) are applied to the alopecic parts of the scalp at intervals of time: (A) or (B) in the morning, (B) or (A) in the evening or one after the other in succession.

EXAMPLE 5

| 6-Amino-1,2-dihydro-1-hydroxy-2-imino-4-diethylamino pyrimidine | 3 g |
|---|---|
| 5-n-Octanoylsalicylic acid | 2 g |
| Propylene glycol | 20 g |
| Ethyl alcohol | 50 g |
| Water q.s | 100 g |

This composition is applied to the alopecic parts of the scalp.

EXAMPLE 6

The following lotion is prepared:

| Minoxidil | 0.54 g |
|---|---|
| 5-n-Octanoylsalicylic acid | 2.2 g |
| Propylene glycol | 22.8 g |
| Ethyl alcohol | 55.1 g |
| Water q.s. | 100 g | and is applied to the alopecic regions of the scalp to promote the fresh growth and to diminish the loss of hair.

EXAMPLE 7

The following lotion is applied to the alopecic regions of the scalp:

| Minoxidil | 5.0 g |
|---|---|
| 5-n-Octanoylsalicylic acid | 1.09 g |
| Ethyl alcohol (50 g) water (50 g) q.s. | 100.0 g |

We claim:

1. A combination of components, which is useful for the treatment of the hair and scalp and is effective for inducing and stimulating hair growth and for decreasing hair loss, comprising:
   (a) a first component (A), comprising a composition containing a physiologically acceptable medium and 6-amino-1,2-dihydro-1-hydroxy-2-imino-4-piperidinopyrimidine or minoxidil; and
   (b) a second component (B), comprising a composition containing a physiologically acceptable medium and 5-n-octanoyl salicylic acid, wherein said components are intended for use as a composition comprising said components or as separate components that are used either simultaneously, successively or intermittently; and wherein minoxidil consists of between 0.05 and 10% by weight of component (A), and 5-n-octanoyl salicylic acid consists of between 0.05 and 10% by weight of component (B).

2. The combination of claim 1, wherein minoxidil is between 0.05 and 5% by weight of component (A).

3. The combination of claim 1, wherein the weight ratio of minoxidil to 5-n-octanoylsalicylic acid is between 1 and 10.

4. The combination of claim 1, wherein said physiologically acceptable medium is selected from the group consisting of a mixture of water and one or more organic solvents, and a mixture of pharmaceutically or cosmetically acceptable organic solvents.

5. The combination of claim 4, wherein said solvents are selected from the group consisting of $C_1$–$C_4$ lower alcohols, alkylene glycols, and mono- and dialkylene glycol alkyl ethers.

6. The combination of claim 1, wherein the physiologically acceptable medium of at least one of components (A) and (B) is thickened by the addition of thickening agents, gelling agents, or both thickening and gelling agents.

7. The combination of claim 1 further comprising in either or both of said components (A) and (B) at least one cosmetically or pharmaceutically acceptable adjuvant selected from the group consisting of preserving agents, complexing agents, colorants, alkalifying agents, acidifying agents, anionic agents, nonionic agents, amphoteric surface-active agents, mixtures of anionic, nonionic, and amphoteric surface-active agents, anionic polymers, cationic polymers, nonionic polymers, amphoteric polymers, and mixtures of anionic, cationic, nonionic and amphoteric polymers.

8. A multicompartment device or kit or outfit comprising component (A) of claim 1 in a first compartment and component (B) of claim 1 in a second compartment.

9. A medicament for the treatment of alopecia consisting of the combination of claim 1 and a carrier suitable for topical application of said medicament to the hair or scalp.

10. A process for the preparation of a medicament for the treatment of alopecia comprising mixing the combination of claim 1 with a carrier that is suitable for the topical application of said medicament to the hair or scalp.

11. The combination of claim 1 comprising a composition containing components (A) and (B).

* * * * *